(12) United States Patent
Rothman et al.

(10) Patent No.: US 7,320,998 B1
(45) Date of Patent: Jan. 22, 2008

(54) CARBOHYDRATE ANALOG INHIBITORS OF ALPHA-AMYLASE

(75) Inventors: Stephen S. Rothman, Berkeley, CA (US); Edmund J. Niedzinskl, Berkeley, CA (US)

(73) Assignee: Chymos Corporation, Berkeley, CA (US)

(*) Notice: Subject to any disclaimer, the term of this patent is extended or adjusted under 35 U.S.C. 154(b) by 556 days.

(21) Appl. No.: 10/888,480

(22) Filed: Jul. 9, 2004

Related U.S. Application Data (60) Provisional application No. 60/487,081, filed on Jul. 11, 2003.

(51) Int. Cl.
*A61K 31/225* (2006.01)
*C07C 67/02* (2006.01)
*C07C 211/00* (2006.01)

(52) U.S. Cl. ............ 514/548; 560/251; 560/252; 564/457

(58) Field of Classification Search ............ None
See application file for complete search history.

(56) References Cited

U.S. PATENT DOCUMENTS 4,174,439 A * 11/1979 Rauenbusch et al. ...... 536/55.3
4,946,925 A * 8/1990 Strohmayer et al. ........ 528/122

OTHER PUBLICATIONS

Fischer S. Influence of treatment with acarbose or glibenclamide on insulin sensitivity in type 2 diabetic patients. *Diabetes Obes Metab.* 2003;5:38-44.

Hauner H. Effect of acarbose on weight maintenance after dietary weight loss in obese subjects. *Diabetes Obes Metab.* 2001;3:423-7.

* cited by examiner

*Primary Examiner*—Paul A. Zucker
(74) *Attorney, Agent, or Firm*—Townsend and Townsend and Crew LLP (57) ABSTRACT

The present invention provides carbohydrate analogs of the formula:

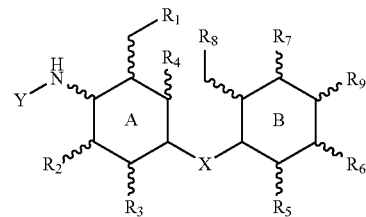

wherein X is $CH_2$, O, or NH, and $R_{1-8}$ are independently H, a short hydrocarbon, a substituted amine, an alcohol, a substituted ether, a substituted amide, a substituted ketone, a substituted carboxylic acid, a short peptide, or a short oligosaccharide, Y is H, a short hydrocarbon, a short peptide, or a short oligosaccharide, and $R_9$ is H, a short hydrocarbon, a substituted amine, an alcohol, a substituted ether, a substituted amide, a substituted ketone, a carboxylic acid, a short peptide, or a short oligosaccharide.

32 Claims, 8 Drawing Sheets

Three Structural Domains of Acarbose
A = Valienamine
B = 4-amino-4,6-dideoxy-α-D-glucose
C = maltose

Synthesis of 2-amino-3-hydroxymethyl-5-(5-methoxy-2,3-dimethyl-cyclohexylamino)-cyclohexanol. 1. A, THF, DMAP 2. $PPh_3$, $CBr_4$, DCM 3. B, DIPEA, DCM 4. TBAF, $H_2O$, THF 5. 2.5% TFA, DCM

FIGURE 7

Synthesis of acetic acid 3,4-diacetoxy-2-(2-amino-3-phenyl-propionylamino)-5-(3,5-dihydroxy-2-hydroxymethyl-4-methyl-cyclohexyloxy)-cyclohexylmethyl ester 1. A1, DIPEA, DCM 2. NaOH, THF 3. A2, HOBt, DCM 4a. NaOH, THF, CsCl$_2$ 4b. B  5. NaBH$_4$, THF  6. TBAF, THF, H$_2$O  7. Ac$_2$O, THF  8. 2.5% TFA, DCM

FIGURE 8

Synthesis of acetic acid 5-amino-2-(3-amino-4-hydroxy-cyclohexylmethyl)-4-({2-[2-(2-amino-propionylamino)-acetylamino]-acetylamino}-methyl)-cyclohexyl ester.
1. A, DMAP, THF 2. CBr4, PPh3, THF, 3. PPh3, THF 4a. t-BuO-K+, THF 4b. B 5. TBAF, H2O, THF 6. Fmoc-Gly-OPfp, DMF 7. piperidine, DMF 8. Fmoc-gly-OH, HOBt, DMF 9. pipieridine, DMF 10. Fmoc-alanine-OH, HOBt, DMF 11. piperidine, DMF 12. 2.5% TFA in DCM 13. Pd, H2, MeOH

CARBOHYDRATE ANALOG INHIBITORS OF ALPHA-AMYLASE

RELATED APPLICATION INFORMATION

This application claims priority to U.S. Provisional Application Ser. No. 60/487,081 filed Jul. 11, 2003, hereby incorporated by reference as if set forth fully herein.

FIELD OF THE INVENTION

The present invention relates to novel carbohydrate analogs and the use of these carbohydrate analogs as inhibitors of α-amylase enzymes.

BACKGROUND OF THE INVENTION

Being overweight is a serious public health problem that greatly increases the risk of many diseases such as diabetes, heart disease, respiratory disease, and even some forms of cancer. More than half the population of the U.S. and other countries in the developed world is overweight and often dangerously so. This situation is thought to be the result of a relatively inactive life style and overeating.

In the U.S. some $60 billion dollars are spent annually attempting to lose weight. Most weight-loss strategies are designed to reduce food intake by diet or by increasing physical activity through exercise. Following this prescription, many people lose weight episodically. But even when such regimens are successful, over 90% of the time the lost weight is regained pound for pound. This failure reflects powerful and complex psychological and physiological drives within us that cause us to take in more calories than we need.

Pharmaceutical companies have developed drugs that are designed to reduce the desire for food, that is, to reduce appetite. Though some of these compounds produce weight loss in experimental animals, they have not been found to be effective in humans thus far. The most effective of them, such as the amphetamines, have serious, treatment limiting side-effects.

Recently, invasive surgical approaches have been added to the weight loss armamentarium for the treatment of gravid obesity. In one method, segments of the small bowel are by-passed to reduce the available absorptive surface, thereby reducing the potential for the absorption of the end products of digestion and their contained calories. In another approach, the size of the gastric lumen is reduced surgically. This reduces food intake by decreasing the holding capacity of the stomach and inducing a sense of satiety as the smaller load of food fills the organ. The risks commonly associated with major surgery and the substantial side-effects of such treatments, such as diarrhea, as well as the need to carefully monitor both the size and character of the meal, make them only useful as a last resort for individuals essentially immobilized by their obesity. They are neither practical nor appropriate for millions of patients whose obesity is not as severe, but who are nonetheless substantially and unhealthily overweight.

A safe and effective means to achieve sustained weight loss for the great majority of overweight people still eludes us.

Figure 1:
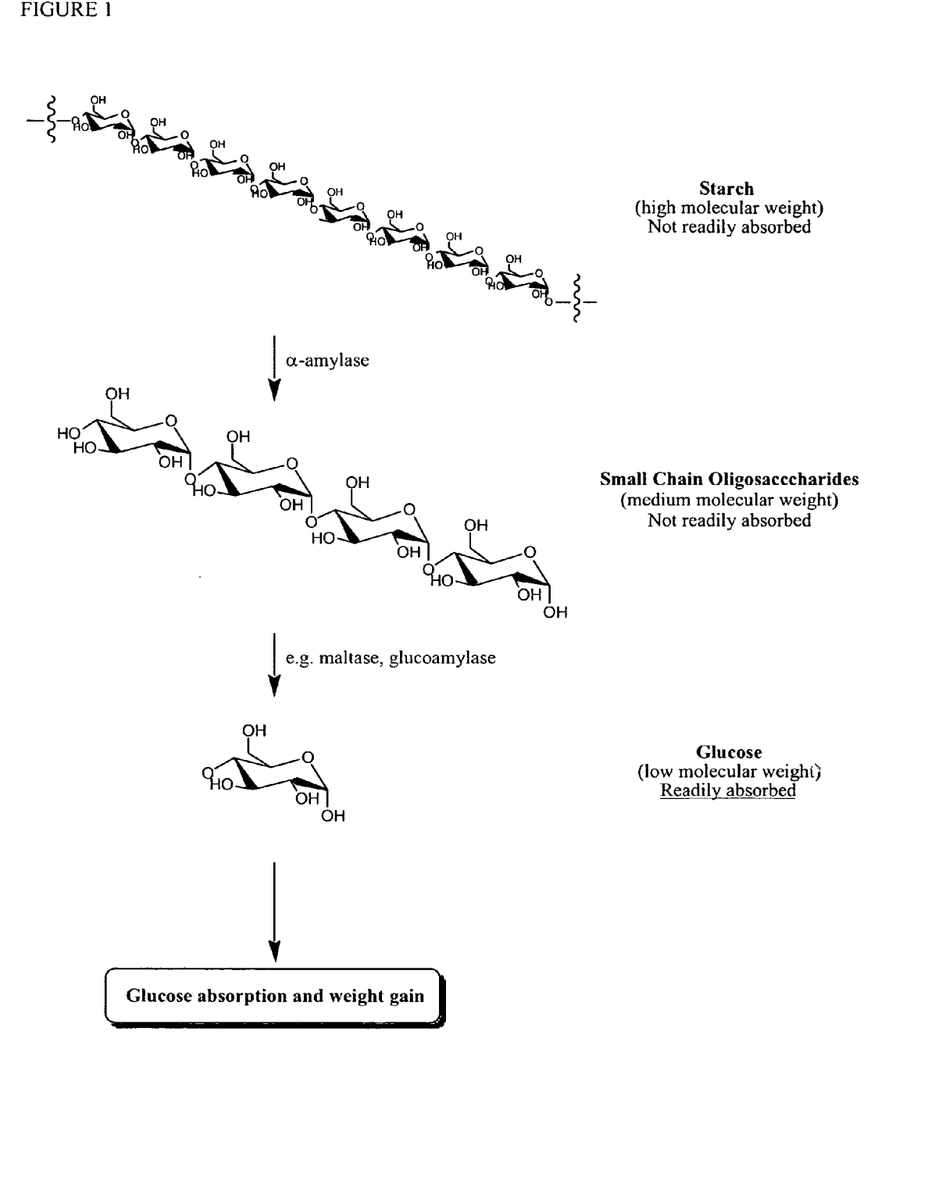
FIG. 1 shows the digestive pathway of starch in a mammal. A starch molecule, a polymer of glucose monomers, is first broken down by α-amylase into smaller polymers. Then, enzymes such as maltase and glucoamylase break these smaller molecules down eventually into glucose. Glucose is then absorbed by the body leading to weight gain.

Starch is the major source of calories in the Western diet. Almost 60% of the food eaten in the U.S. and Europe is in the form of carbohydrates, such as starches and simple sugars. Starch is a branched-chain or linear polymer of glucose molecules (FIG. 1). Its digestion in humans and other mammals is the responsibility of an enzyme called α-amylase. Alpha-amylase is a member of family 13 in a group of sixty-two families of enzymes referred to as glycosylhydrolases. Alpha-amylase breaks the α-1,4-glycosidic bond between adjacent glucose molecules in the starch polymer. Through repetitive chemical reactions, α-amylase reduces a starch molecule to smaller and smaller polymers, and eventually reduces it to small glucose polymers, mostly dimers, trimers, and α-limit dextrins (short polymers that contain a branch point such as a α-1,6 glycosidic bond between glucose molecules) (FIG. 1). These small polymers are then reduced to glucose monomers in the small intestines by the enzymes maltase and glucoamylase (FIG. 1). The resulting glucose is absorbed into blood.

In humans, α-amylase is secreted by two glands, the salivary glands and the pancreas. Salivary and pancreatic α-amylase are very similar, though distinct gene products, each with several isoenzymes. The salivary glands release amylase into the mouth, while the pancreas releases it into the small intestine. Each subtype is responsible for about 50% of the starch digestion that occurs in the body.

Inhibitors of various glycosylhydrolases have been known for over 20 years and are found naturally in a variety of plants, fungi, and bacteria. None of these natural inhibitors are specific for α-amylase or particularly effective against this enzyme. There are two types of natural glycosylhydrolase inhibitors: non-competitive and competitive. Competitive inhibitors bind at the active site of the enzyme, and displace the natural substrate. The majority of competitive inhibitors are small sugar monomers or polymers that are chemically similar to the natural substrates they displace. The first generation of these competitive inhibitors are natural products that are found primarily in bacteria and fungi.

The non-competitive inhibitors, on the other hand, do not bind at the active catalytic site of the enzyme and hence do not displace the natural substrate. These non-competitive inhibitors are primarily proteins that are found in various beans and legumes. In humans, acid in the stomach and proteolytic enzymes in the small bowel destroy protein-based inhibitors, rendering them ineffective as inhibitors of glycosylhydrolase enzymes.

Although the natural sugar-based inhibitors do not suffer from this drawback, those that have been discovered thus far are ineffective as inhibitors of α-amylase activity. These natural sugar-based inhibitors are effective against a variety of non-amylase glycosylhydrolases found in the small intestines, such maltase, sucrase, lactase, and glucoamylase.

Figure 2:
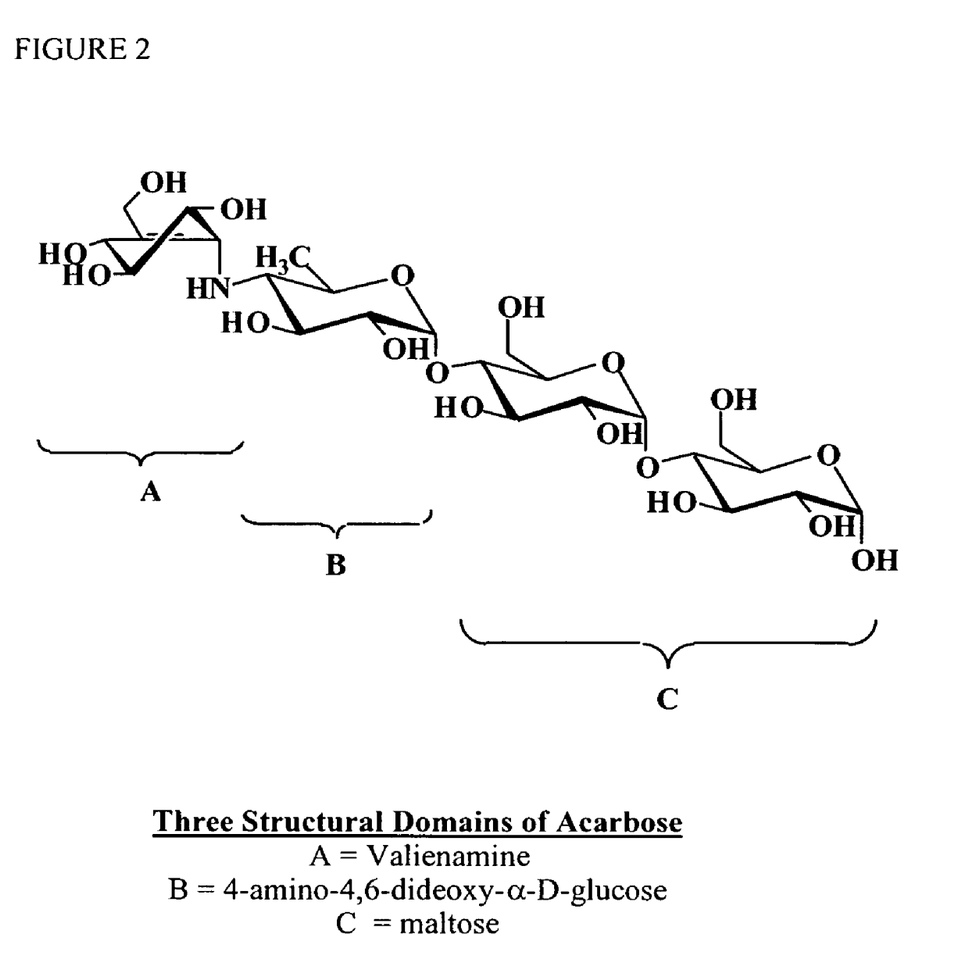
FIG. 2 shows the prior art glycosylhydrolase inhibitor, acarbose. Acarbose is comprised of three structural domains: valienamine (region A), 4-amino-4,6-dideoxy-α-D-glucose (region B), and maltose (region C).

Glycosylhydrolase inhibitors were originally considered for agriculture uses as natural pesticides to protect plant seeds from insect infestation, but their main commercial use to date has been in the treatment of diabetes. The most well known of these compounds is acarbose, marketed by Bayer as Precose. Acarbose is a tetramer comprised of valienamine (A), 4-amino-4,6-dideoxy-α-D-glucose (B), and maltose (a glucose dimer) (C) sub-units (FIG. 2). Acarbose acts by decreasing the sharp increase in blood glucose concentration seen following the ingestion of a starch or sugar containing meal by patients with type 2 diabetes. This delay in absorption is thought to help prevent the serious side-effects of diabetes produced by highly elevated blood sugar levels.

Although acarbose is safe and almost quantitatively eliminated in feces (that is, it is not readily absorbed by the body), acarbose and similar inhibitors only reduce the rate at which monosaccharides appear in blood. In the end, the whole caloric load is absorbed. This, of course, makes them useless as a means of weight loss. The reason for their ineffectiveness is that even for the enzymes that they most strongly inhibit, such as lactase and glucoamylase, their inhibitory action is insufficient to prevent the breakdown of small sugar polymers into absorbable monosaccharides before they pass out of the small bowel.

In addition, there are also significant side-effects associated with acarbose use. To the extent that acarbose and other similar inhibitors are able to prevent the final stage in starch digestion, they leave relatively high concentrations of undigested substrates, non-absorbable disaccharides and small polymers, in the intestines. This causes the osmotic movement of water into the gut lumen and produces diarrhea in about ⅓ of the patients taking acarbose. Furthermore, a successful inhibitor of this type introduces relatively large quantities of small sugars into the large bowel where they can be metabolized and fermented within bacterial cells. Some of the products of bacterial action, such as lactic acid, are absorbed and their caloric content made available to the patient. Significant amounts gas ($CO_2$) may also be produced, and about ⅓ of the patients taking acarbose complain of gas.

SUMMARY OF THE INVENTION

The present invention provides a method of inhibiting starch digestion itself rather than the final stages of carbohydrate digestion, through the inhibition of the enzyme α-amylase. By inhibiting starch digestion, both the osmotic and fermentation side-effects found with other glycosylhydrolase inhibitors can be minimized. Because starch is a large molecule, it is not particularly osmotically active and hence its presence in the small bowel does not produce an osmotic diarrhea. Also, when the large starch polymers enter the colon, bacteria are unable to "absorb" them for intracellular fermentation and metabolism and any extracellular bacterial enzymatic reactions are limited by the relatively small surface to volume ratio of the large starch polymers.

This approach to weight loss, unlike diet, drugs, or exercise, does not attempt to reduce food intake or increase energy use. Rather, it seeks to manage the utilization of food after ingestion. By reducing starch digestion, carbohydrate utilization and caloric load are reduced. When starch digestion is effectively inhibited, starches and the calories associated with them simply pass through the intestines like dietary cellulose, unused and unabsorbed. This will allow patients to lose weight, while consuming a normal diet and fulfilling their desire for starchy foods such as bread, crackers, potatoes, rice, other grains, various beans, and of course "junk" food. In addition, being able to eat starchy foods makes other dietary restrictions, such as low fat diets, far easier to tolerate.

The current invention, in one aspect, governs the digestion of starches by providing molecules that are inhibitors of α-amylase, the enzyme responsible for the digestion of starches in humans and other mammals. The α-amylase inhibitors of the present invention are carbohydrate analogs. These inhibitors are based on the structures shown in FIG. 3 and described more fully below.

DETAILED DESCRIPTION OF VARIOUS EMBODIMENTS OF THE INVENTION

In one aspect, the present invention provides novel carbohydrate analogs having formula:

wherein X is NH, $CH_2$, or O; $R_1$, $R_2$, $R_3$, $R_4$, $R_5$, $R_6$, $R_7$, $R_8$ are each independently selected from the group consisting of H, an alkyl group having 1 to 6 carbon atoms, an alkenyl group having 1 to 6 carbon atoms, an alkynyl group having 1 to 6 carbon atoms, a halogen-substituted alkyl group having 1 to 6 carbon atoms, OH, NR'R", wherein R' and R" are each independently H or an alkyl group having 1 to 3 carbon atoms, NR'C(O)R", wherein R' is H or an alkyl group having 1 to 3 carbon atoms and R" is an alkyl group having 1 to 2 carbon atoms, R'NR"R'", wherein R' is an alkyl group having 1 to 3 carbon atoms and R" and R'" are each independently H or an alkyl group having 1 to 3 carbon atoms, R'NR"C(O)R'", wherein R' is an alkyl group having 1 to 3 carbon atoms, R" is H or an alkyl group having 1 to 3 carbon atoms, and R' is an alkyl group having 1 to 2 carbon atoms, ROH, wherein R is an alkyl group consisting of 1 to 3 carbon atoms, OR', wherein R' is an alkyl group having 1 to 4 carbon atoms, R'OR", wherein R' and R" are each independently an alkyl group having 1 to 4 carbon atoms, C(O)NR'R", wherein R' and R" are each independently H or an alkyl group consisting of 1 to 3 carbon atoms, OC(O)

NR'R", wherein R' and R" are each independently H or an alkyl group consisting of 1 to 3 carbon atoms, R'C(O) NR"R'", wherein R', R", and R'" are each independently an alkyl group having 1 to 3 carbon atoms, C(O)R', wherein R' is H or an alkyl group having 1 to 4 carbon atoms, R'C(O)R", wherein R' is an alkyl group having 1 to 4 carbon atoms, and R" is H or an alkyl group having 1 to 4 carbon atoms, R'OC(O)R", wherein R' is an alkyl group having 1 to 3 carbon atoms, and R" is H or an alkyl group having 1 to 3 carbon atoms, C(O)OR', wherein R' is H or an alkyl group having 1 to 4 carbon atoms, R'C(O)OR", wherein R' is an alkyl group having 1 to 4 carbon atoms and R" is H or an alkyl group having 1 to 4 carbon atoms, a peptide consisting of 1 to 6 amino acids, and an oligosaccharide consisting of 1 to 6 sugar monomers; Y is selected from the group consisting of H, an alkyl group having 1 to 6 carbon atoms, a peptide consisting of 1 to 6 amino acids, and an oligosaccharide consisting of 1 to 6 sugar monomers; and $R_9$ is selected from the group consisting of H, an alkyl group having 1 to 6 carbon atoms, OH, NR'R", wherein R' and R" are each independently H or an alkyl group having 1 to 3 carbon atoms, ROH, wherein R is an alkyl group consisting of 1 to 3 carbon atoms, OR', wherein R' is an alkyl group having 1 to 4 carbon atoms, R'OR", wherein R' and R" are each independently an alkyl group having 1 to 4 carbon atoms, C(O)NR'R", wherein R' and R" are each independently H or an alkyl group consisting of 1 to 3 carbon atoms, R'C(O)NR"R'", wherein R' is an alkyl group having 1 to 3 carbon atoms and R" and R'" are each independently H or an alkyl group having 1 to 3 carbon atoms, C(O)R', wherein R' is H or an alkyl group having 1 to 4 carbon atoms, R'C(O)R", wherein R' is an alkyl group having 1 to 4 carbon atoms, and R" is H or an alkyl group having 1 to 4 carbon atoms, C(O)OR', wherein R' is H or an alkyl group having 1 to 4 carbon atoms, R'C(O)OR", wherein R' is an alkyl group having 1 to 4 carbon atoms and R" is H or an alkyl group having 1 to 4 carbon atoms, a peptide consisting of 1 to 6 amino acids, and an oligosaccharide consisting of 1 to 6 sugar monomers. A halogen-substituted alkyl group is an alkyl group that is substituted on any carbon atom with a halogen atom selected from the group consisting of bromine, chlorine, and fluorine. Alkyl and alkenyl groups can be branched or straight chain alkyl groups. Stereochemically, these substituents are situated on either the down side (the α face) or the up side (the β face) of the ring. In further aspects of the present invention, compounds are provided in which at least one, at least two, at least three, at least four, at least five, at least six, or at least seven of the functional groups $R_1$, $R_2$, $R_3$, $R_4$, $R_5$, $R_6$, $R_7$, or $R_8$ are OH. Compounds are also provided in which at least one, at least two, at least three, at least four, or at least five of the functional groups $R_1$, $R_2$, $R_3$, $R_4$, $R_5$, $R_6$, $R_7$, or $R_8$ are H.

The types of sugar monomers contemplated by the present invention include naturally-occurring pentoses and hexoses. For example, the sugar monomers of the present invention can be ribose, glucose, mannose, galactose, fructose, xylose, and alcoholic sugars. Sugar monomers of the present invention are bonded to each other in the manner of naturally occurring sugar polymers, such as, for example, through α(1→4) bonds, α(1→6) bonds in the case of glucose monomers, β glycosidic bonds, amino bonds, and permutations of glycosidic bonds (for example, 1,5 or 1,3 bonds). The oligosaccharides of the present invention can consist of polymers of the same or of different sugar monomers. Similarly, the amino acid substituents contemplated by the present invention include naturally-occurring D and L amino acids. The invention also contemplates peptide substituents consisting of combinations of these amino acids. These peptide substituents can consist of polymers of the same or of different amino acids.

All stereoisomers of the compounds of the present invention are contemplated, either as an admixture or in pure or substantially pure form. The compounds of the present invention embrace all possible stereoisomers and their mixtures. The present invention particularly includes the racemic forms and the isolated optical isomers. The racemic forms can be resolved by physical methods, such as, for example, fractional crystallization, separation or crystallization of diastereomeric derivatives, or chiral column chromatography. The individual optical isomers can be obtained from the racemates by conventional methods, such as, for example, salt formation with an optically active acid followed by crystallization.

In another aspect of the present invention, pharmaceutically acceptable salts of the carbohydrate analogs disclosed herein are provided. Pharmaceutically acceptable salts include, for example, alkali metal salts (e.g., potassium or sodium salts), alkaline earth salts (e.g., calcium or magnesium salts), ammonium salts, salts of amines, salts of carboxylic acids, salts of sulfates, salts of phosphates, methanesulfonate salts, ethanesulfonate salts, bisulfate salts, acid citrate salts, lactate salts, tartrate salts, gluconate salts, succinate salts, salicylate salts, hydrochloride salts, hydrobromide salts, and hydroiodide salts. A large variety of pharmaceutically acceptable salts are well-known in the art and the foregoing description is not meant to be limiting.

Generally, the carbohydrate analogs of the present invention can be synthesized using solid or solution phase chemistry. Solid-phase chemistry can simplify the synthesis of a of compounds by derivatizing a substrate while it is attached to an insoluble polymeric support. When the substrate is linked to an insoluble polymeric support, these chemical reactions can be conducted and the by-products can be removed by washing the polymer-bound substrate. For example, silicon-based protecting groups are commonly used in synthetic chemistry. These protecting groups are removed by treating the compound with an organic fluoride salt, such as tetrabutylammonium fluoride. In solution-phase chemistry, the by-product of this reaction may be difficult to separate from the desired compound. In solid-phase chemistry, the by-products are simply washed away from the polymer bound substrate by filtration. After the required synthetic steps are completed, the substrate is cleaved from the polymer and collected by filtration.

Figure 5:
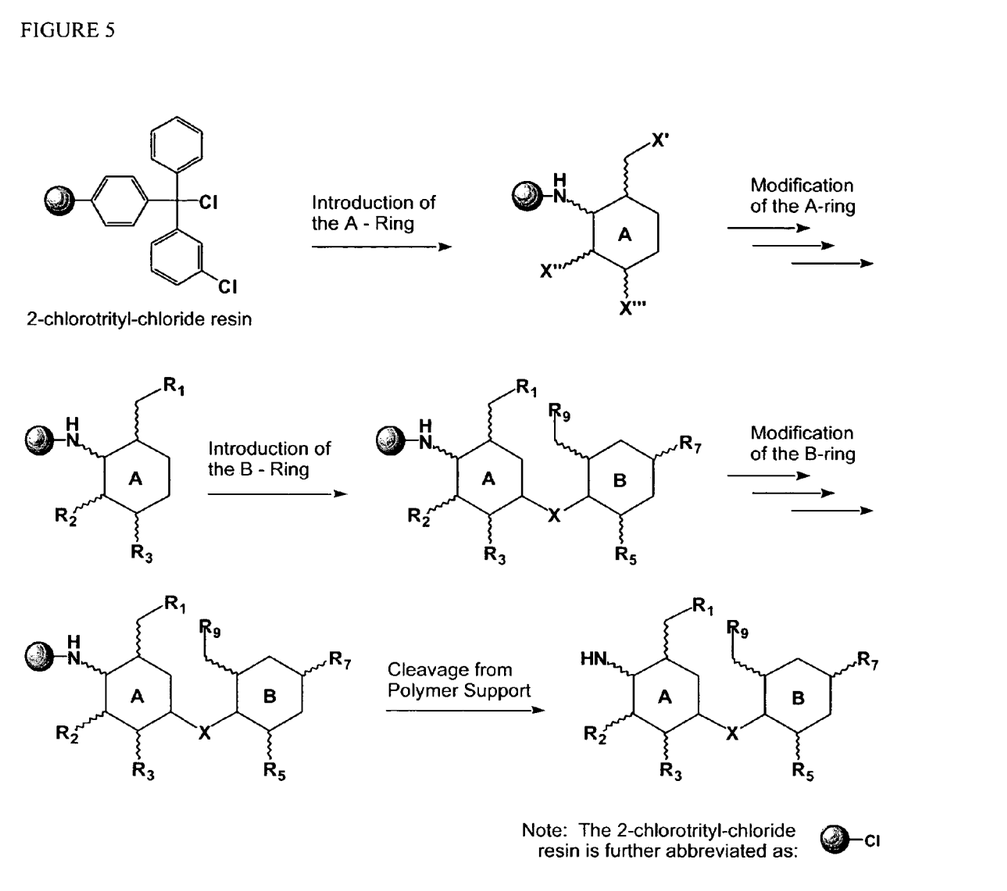
FIG. 5 shows a general outline of a solid-phase chemical synthesis of some of the inhibitors of the present invention. The polystyrene resin is depicted by the shaded circle.

An outline of a strategy that is used to synthesize the carbohydrate analogs of the present invention is shown in FIG. 5. This strategy builds upon the commercially available 2-chlorotrityl-chloride resin. This resin tolerates a wide range of chemical reactions and the product can be removed from the polymer in mildly acidic conditions. In the first stage of the synthesis, a hexane derivative ("the A ring") precursor is covalently attached to the polymeric support. The A ring is modified to introduce the desired functional groups using chemistry that is compatible with solid phase techniques (stage two). When these modifications are complete, the second hexane derivative ("the B ring") precursor is added to the polymer-bound A ring (stage three). After the B-ring precursor is conjugated similar chemical reactions are used to manipulate the substituents on the B ring (stage four). The target compound is cleaved from the resin using mild chemistry (for example, by using trifluoroacetic acid in dichloromethane) and the compound is obtained by washing the solid phase resin with an appropriate solvent (stage five).

Some chemical reactions are not compatible with solid phase chemistry (e.g., hydrogenation reactions that require the presence of a heterogeneous catalyst). These manipulations must be conducted after the inhibitor is cleaved from the solid support. The purity of the carbohydrate derivatives obtained can determined, for example, by HPLC and/or $^1$H-NMR.

In a further aspect of the present invention, the compounds disclosed herein demonstrate an $IC_{50}$, a value at which 50% of the activity of human salivary α-amylase is inhibited, that is less than $1\times10^{-4}$ M. In a preferred embodiment, this $IC_{50}$ is less than $5\times10^{-4}$ M. In a further preferred embodiment, this $IC_{50}$ is less than $1\times10^{-6}$ M. In a further preferred embodiment, this $IC_{50}$ is less than $1\times10^{-8}$ M. In a further preferred embodiment, this $IC_{50}$ is less than $1\times10^{-10}$ M. In a further preferred embodiment, this $IC_{50}$ is less than $1\times10^{-12}$ M. In another aspect of the present invention, the compounds disclosed herein demonstrate an $IC_{50}$ toward human pancreatic α-amylase that is less than $1\times10^{-4}$ M. In a preferred embodiment, this $IC_{50}$ is less than $5\times10^{-4}$ M. In a further preferred embodiment, this $IC_{50}$ is less than $1\times10^{-6}$ M. In a further preferred embodiment, this $IC_{50}$ is less than $1\times10^{-8}$ M. In a further preferred embodiment, this $IC_{50}$ is less than $1\times10^{-10}$ M. In a further preferred embodiment, this $IC_{50}$ is less than $1\times10^{-12}$ M.

In a further embodiment, inhibitors are provided that have a higher $IC_{50}$ toward α-amylase than toward other glucohydrolase enzymes, such as maltase, lactase, sucrase, and glucoamylase. In another aspect, these inhibitors are polymers having at least four or at least five or more sugar or sugar analog units. The totaling of polymer units discussed here includes any derivatized cyclohexanes as polymer units. Additional units are composed of sugar monomers.

The $IC_{50}$ for an inhibitor and an enzyme is the concentration of the inhibitor that is required to decrease the native activity of the enzyme by 50%. An $IC_{50}$ of an inhibitor for a particular enzyme (e.g., pancreatic α-amylase, salivary α-amylase, maltase, and sucrase) can be measured using commercially available (e.g., from Sigma Chemical Co.) in vitro assays that are adapted for analysis using a 96-well microplate reader. Generally, the enzymatic hydrolysis of a carbohydrate is determined by incubating a colorimetric substrate with the enzyme. As the enzyme hydrolyses the substrate, the absorbance of the substrate decreases and the absorbance of the product increases. The rate at which the substrate absorbance decreases or product absorbance increases is considered the native activity of the enzyme. The $IC_{50}$ of an inhibitor is measured by adding various concentrations of the inhibitor to the enzyme prior to the addition of the calorimetric substrate. The $IC_{50}$ value is obtained by plotting the rate of carbohydrate hydrolysis in the presence of the inhibitor versus the concentration of the inhibitor.

Figure 4:
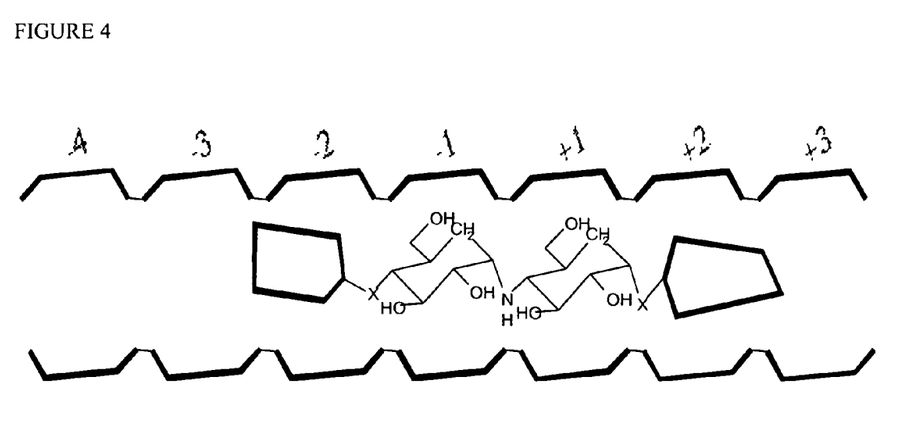
FIG. 4 shows a molecule of the present invention inside the active site (the $(\beta/\alpha)_8$ barrel) of α-amylase.

Not to be bound by theory, it is believed that the inhibitors of the present invention enter the active site of α-amylase (as shown in FIG. 4) thus excluding the natural substrate starch and preventing α-amylase from catalyzing the breakdown of starch.

Figure 3:
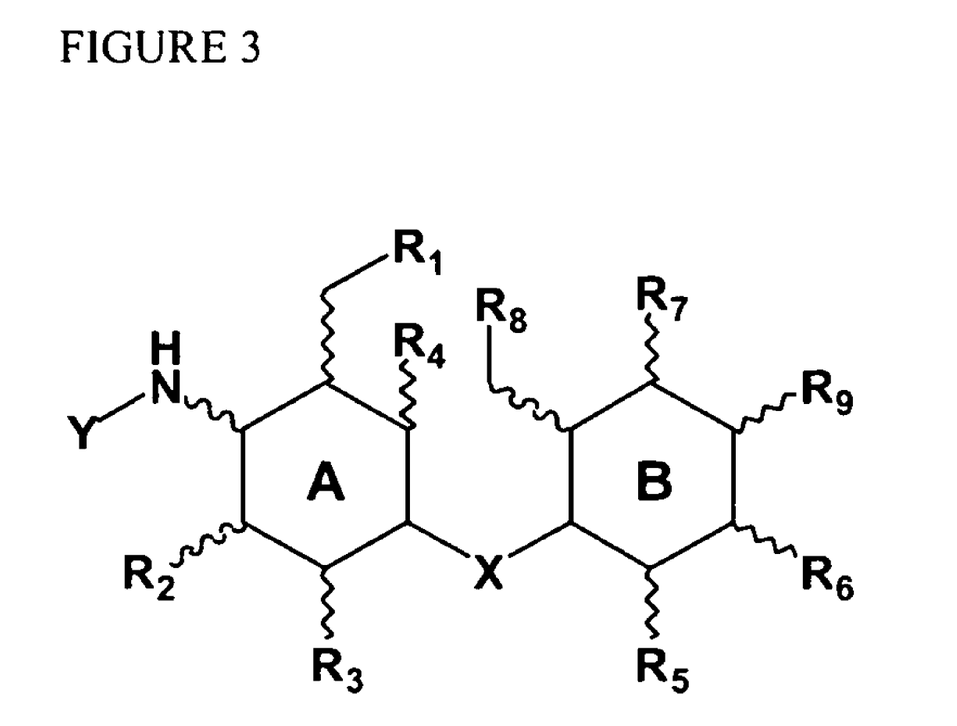
FIG. 3 is a representation of the basic core structure around which the inhibitors of the present invention are designed. As described more fully herein, the inhibitors of the present invention are derivatives of these core structures.

FIG. 3 shows the basic core structure of the inhibitors of the present invention. As can be seen, this core structure is composed of a bicyclohexane structure which is two derivatized cyclohexane rings linked together through a single atom bridge.

In another embodiment, the present invention provides a method of administering carbohydrate analogs according to the present invention to a mammal in an α-amylase inhibitory effective amount. In a further embodiment, a method of inhibiting α-amylase activity in a human comprised of orally administering to the human an α-amylase inhibitory effective amount of a compound having an $IC_{50}$ of less than $1\times10^{-4}$ M, less than $5\times10^{-4}$ M, less than $1\times10^{-6}$ M, less than $1\times10^{-8}$ M, less than $1\times10^{-10}$ M, or less than $1\times10^{-12}$ M toward the human pancreatic or salivary α-amylase enzyme is provided.

An α-amylase inhibitory effective amount comprises about 10 ng to about 1 g per day, preferably about 1 mg to about 100 mg per day, and more preferably about 1 mg to about 25 mg per day of a carbohydrate analog or a mixture of analogs. The carbohydrate analogs can be administered to a mammal in a pharmaceutically effective form including combined with excipients, diluents, or carriers. The compounds can be administered in the form of powders mixed with or sprinkled on food, food additives, solutions, suspensions or slurries with water, or other liquids, pastes, tablets (including pills, lozenges, chewable tablets, and granules inside capsules), gel capsules, liquid formulations, chewing gums, and suppositories which may contain flavoring or coloring agents, for immediate-, delayed-, sustained-, pulsed-, or controlled-release applications. For example, the compounds of the present invention may be mixed with excipients such as microcrystalline cellulose, lactose, sodium citrate, calcium carbonate, dibasic calcium phosphate and glycine, disintegrants such as starch, sodium starch glycollate, granulation binders, sucrose, gelatin, and acacia. Antioxidants and agents that improve flavoring may also be included. Furthermore, the compounds of the present invention may be administered by any suitable route, including oral and rectal routes.

EXAMPLE 1

Figure 6:
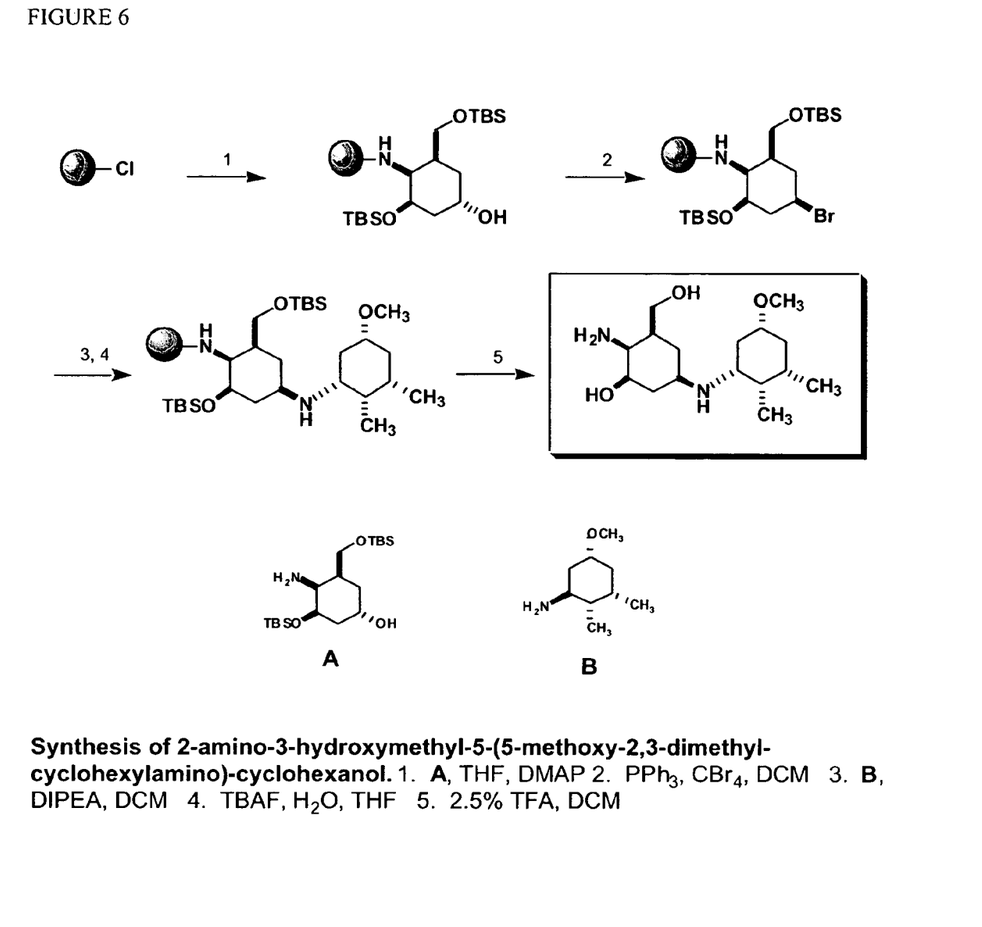
FIG. 6 diagrams steps in the solid-phase chemical synthesis of 2-amino-3-hydroxymethyl-5-(5-methoxy-2,3-dimethyl-cyclohexylamino)-cyclohexanol, a carbohydrate analog of the present invention.

A carbohydrate analog (2-amino-3-hydroxymethyl-5-(5-methoxy-2,3-dimethyl-cyclohexylamino)-cyclohexanol) having the following structure:

is synthesized according to the synthetic strategy diagrammed in FIG. 6. The A ring substituents are attached to the polymeric support by nucleophilic substitution of the benzylic chloride with the primary amine. The secondary alcohol is then converted to the bromide using mild bromination conditions with triphenylphosphine and carbon tetrabromide. The B ring is added by displacing the bromide with a secondary amine. The protection groups are then removed using tetrabutylammonium fluoride (TBAF) and the inhibitor is collected by treating the polymer with a 2.5% solution of trifluoroacetic acid and rinsing the polymer with solvent.

EXAMPLE 2

Figure 7:
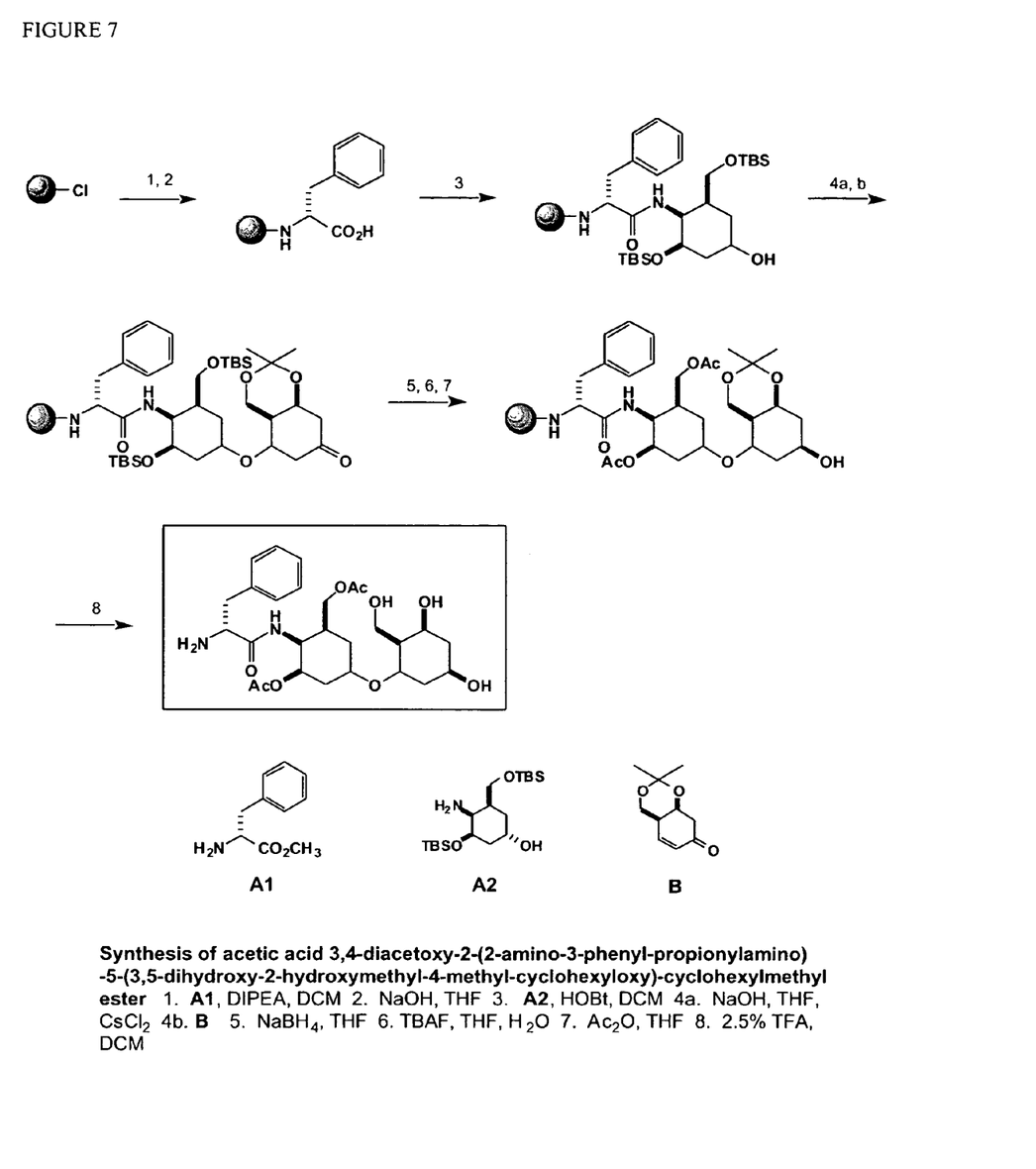
FIG. 7 diagrams steps in the solid-phase chemical synthesis of acetic acid 3,4-diacetoxy-2-(2-amino-3-phenyl-propionylamino)-5-(3,5-dihydroxy-2-hydroxymethyl-4-methyl-cyclohexyloxy)-cyclohexylmethyl ester, a carbohydrate analog of the present invention.

A carbohydrate analog (acetic acid 3,4-diacetoxy-2-(2-amino-3-phenyl-propionylamino)-5-(3,5-dihydroxy-2-hy- droxymethyl-4-methyl-cyclohexyloxy)-cyclohexylmethyl ester) having the following structure:

is synthesized according to the synthetic strategy diagrammed in FIG. 7. Rather than directly linking the A ring to the polymer, an amino acid derivative is linked to the polymer by alkylation of the benzylic chloride on the polymeric support with an amino acid derivative. This strategy represents a simple method to introduce an amino acid onto the A ring in the early stages of the synthesis. After treating the polymer bound amino ester with base, the A ring precursor is introduced through the formation of an amide bond using HOBt. After treating the polymer bound A ring with mild base and cesium chloride, the B-ring is added through a conjugate addition to the α,β-unsaturated carbonyl. The ketone is reduced with sodium borohydride and the silicon protecting groups are then removed with tetrabutylammonium fluoride. The free alcohols are finally acetylated with acetic anhydride under basic conditions. The inhibitor is collected by treating the polymer with a 2.5% solution of trifluoroacetic acid and rinsing the polymer with solvent.

EXAMPLE 3

Figure 8:
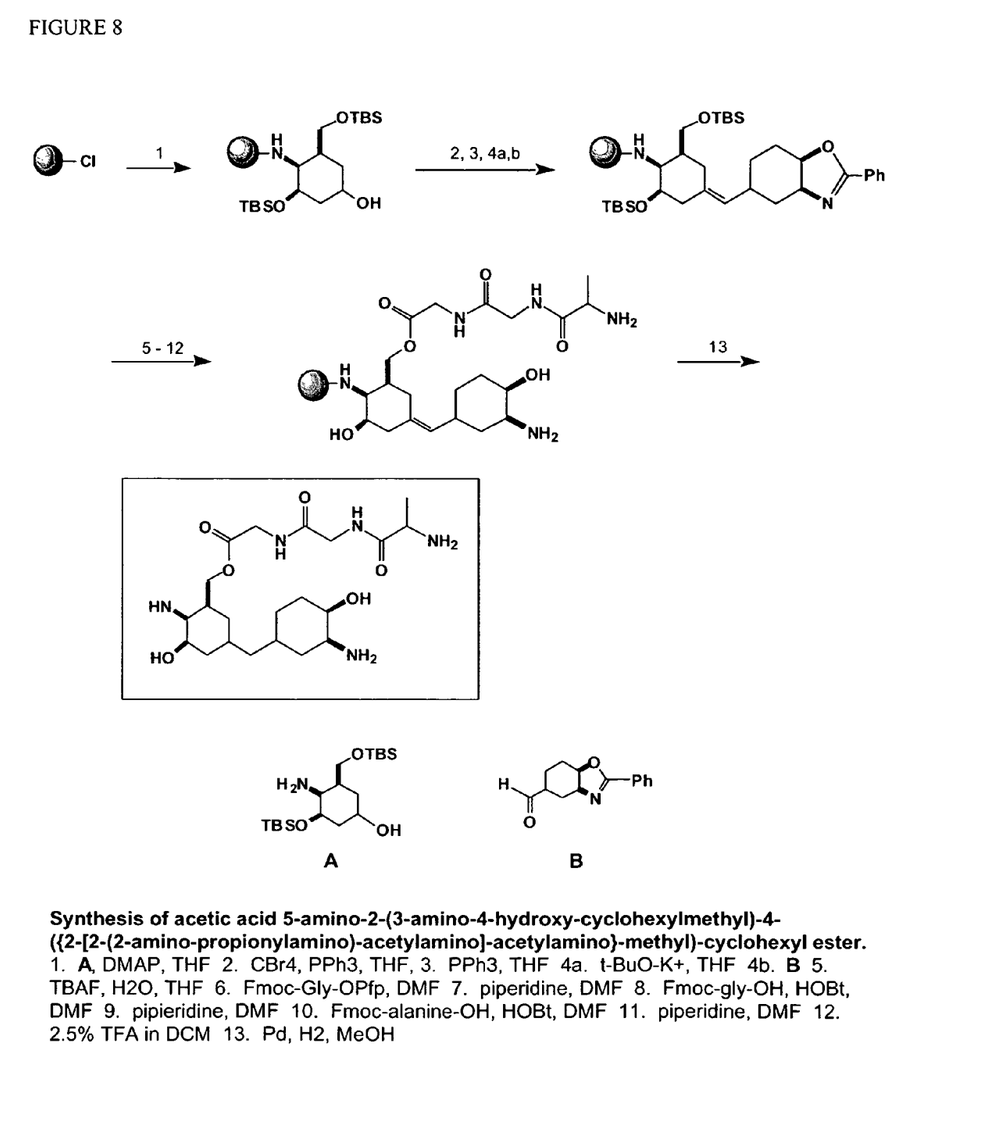
FIG. 8 diagrams steps in the solid-phase chemical synthesis of acetic acid 5-amino-2-(3-amino-4-hydroxy-cyclohexylmethyl)-4-({2-[2-(2-amino-propionylamino)-acetylamino]-acetylamino}-methyl)-cyclohexyl ester, a carbohydrate analog of the present invention.

A carbohydrate analog (acetic acid 5-amino-2-(3-amino-4-hydroxy-cyclohexylmethyl)-4-({2-[2-(2-amino-propionylamino)-acetylamino]-acetylamino}-methyl)-cyclohexyl ester) having the following structure:

is synthesized according to the synthetic strategy diagrammed in FIG. 8. The A ring precursor is attached to the polymeric support by nucleophilic substitution of the benzylic chloride with the primary amine. The secondary alcohol is converted to the bromide using mild bromination conditions using triphenylphosphine and carbon tetrabromide. The bromide is subsequently converted to the phosphonate salt by treatment with triphenylphosphine. Treating the phosphonate salt with potassium tert-butoxide generates the carbanion intermediate, which immediately reacts with the aldehyde of the carbonyl of the B-ring precursor to form an alkene. The primary and secondary alcohols are then deprotected with TBAF, and a tripeptide is regioselectively added to the primary alcohol using standard solid-phase peptide synthesis techniques. The polymer bound substrate is then treated with dilute acid, which deprotects the 1,2-amino alcohol and cleaves the precursors from the polymer support. The double bond is then reduced in situ using hydrogen gas and a palladium catalyst. The reaction is filtered to separate the catalyst from the inhibitor.

What is claimed is:

1. A method of reducing caloric utilization in a human comprised of orally administering to the human an α-amylase inhibitory effective amount of a bicyclohexane derivative having an in vitro $IC_{50}$ of less than $1 \times 10^{-4}$ M toward human pancreatic or salivary α-amylase enzyme.

2. The method of claim 1 where the in vitro $IC_{50}$ of the compound is less than $1 \times 10^{-4}$ M toward human pancreatic α-amylase enzyme.

3. The method of claim 1 where the in vitro $IC_{50}$ of the compound is less than $1 \times 10^{-4}$ M toward human salivary α-amylase enzyme.

4. The method of claim 1 where the in vitro $IC_{50}$ of the compound is less than $5 \times 10^{-4}$ M toward human pancreatic or human salivary α-amylase enzyme.

5. A method of inhibiting α-amylase activity in a human comprised of orally administering to the human an α-amylase inhibitory effective amount of a bicyclohexane derivative having an in vitro $IC_{50}$ of less than $1 \times 10^{-4}$ M toward human pancreatic or salivary α-amylase enzyme.

6. The method of claim 5 where the in vitro $IC_{50}$ of the compound is less than $1 \times 10^{-4}$ M toward human pancreatic α-amylase enzyme.

7. The method of claim 5 where the in vitro $IC_{50}$ of the compound is less than $1 \times 10^{-4}$ M toward human salivary α-amylase enzyme.

8. The method of claim 5 where the in vitro $IC_{50}$ of the compound is less than $5 \times 10^{-4}$ M toward human pancreatic or human salivary α-amylase enzyme.

9. A compound of the formula:

wherein X is $CH_2$,
at least two of $R_1$, $R_2$, $R_3$, $R_4$, $R_5$, $R_6$, $R_7$, $R_8$ are each H; or at least two of $R_1$, $R_2$, $R_3$, $R_4$, $R_5$, $R_6$, $R_7$, $R_8$ are each OH; the remaining functional groups are each independently selected from the group consisting of H; an alkyl group having 1 to 6 carbon atoms; an alkenyl group having 1 to 6 carbon atoms; an alkynyl group having 1 to 6 carbon atoms; a halogen-substituted alkyl group having 1 to 6 carbon atoms; OH; NR'R", wherein R' and R" are each independently H or an alkyl group having 1 to 3 carbon atoms; NR'C(O)R", wherein R' is H or an alkyl group having 1 to 3 carbon atoms and R" is an alkyl group having 1 to 2 carbon atoms; R'NR"R'", wherein R' is an alkyl group having 1 to 3 carbon atoms and R" and R'" are each independently H or an alkyl group having 1 to 3 carbon atoms; R'NR"C(O)R''', wherein R' is an alkyl group having 1 to 3 carbon atoms, R" is H or an alkyl group having 1 to 3 carbon atoms, and R''' is an alkyl group having 1 to 2 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group having 1 to 3 carbon atoms; OC(O)NR'R", wherein R' and R" are each independently H or an alkyl group consisting of 1 to 3 carbon atoms; R'C(O)NR"R''', wherein R' is an alkyl group having 1 to 3 carbon atoms and R" and R''' are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms and R" is H or an alkyl group having 1 to 4 carbon atoms; R'OC(O)R", wherein R' is an alkyl group having 1 to 3 carbon atoms, and R" is H or an alkyl group having 1 to 3 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms; a peptide consisting of 1 to 6 amino acids; and an oligosaccharide consisting of 1 to 6 sugar monomers, Y is selected from the group consisting of H, an alkyl group having 1 to 6 carbon atoms, a peptide consisting of 1 to 6 amino acids, and an oligosaccharide consisting of 1 to 6 sugar monomers, and $R_9$ is selected from the group consisting of H, an alkyl group having 1 to 6 carbon atoms; OH; NR'R", wherein R' and R" are each independently H or an alkyl group having 1 to 3 carbon atoms; R'NR"R''', wherein R' is an alkyl group having 1 to 3 carbon atoms and R" and R''' are each independently H or an alkyl group having 1 to 3 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; R'C(O)NR"R''', wherein R' is an alkyl group having 1 to 3 carbon atoms and R" and R''' are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms; a peptide consisting of 1 to 6 amino acids; and an oligosaccharide consisting of 1 to 6 sugar monomers, wherein at least one of Y or $R_9$ is an oligosaccharide consisting of 1 to 6 sugar monomers, or a pharmaceutically acceptable salt thereof.

10. A compound according to claim 9 wherein at least two of $R_1$, $R_2$, $R_3$, $R_4$, $R_5$, $R_6$, $R_7$, $R_8$ are each H or OH; the remaining functional groups are each independently selected from the group consisting of H; an alkyl group having 1 to 6 carbon atoms; an alkenyl group having 1 to 6 carbon atoms; an alkynyl group having 1 to 6 carbon atoms; a halogen-substituted alkyl group having 1 to 6 carbon atoms; OH; NR'R", wherein R' and R" are each independently H or an alkyl group having 1 to 3 carbon atoms; NR'C(O)R", wherein R' is H or an alkyl group having 1 to 3 carbon atoms and R" is an alkyl group having 1 to 2 carbon atoms; R'NR"R''', wherein R' is an alkyl group having 1 to 3 carbon atoms and R" and R''' are each independently H or an alkyl group having 1 to 3 carbon atoms; R'NR"C(O)R''', wherein R' is an alkyl group having 1 to 3 carbon atoms, R" is H or an alkyl group having 1 to 3 carbon atoms, and R''' is an alkyl group having 1 to 2 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; OC(O)NR'R", wherein R' and R" are each independently H or an alkyl group consisting of 1 to 3 carbon atoms; R'C(O)NR"R''', wherein R' is an alkyl group having 1 to 3 carbon atoms and R" and R''' are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; R'OC(O)R", wherein R' is an alkyl group having 1 to 3 carbon atoms, and R" is H or an alkyl group having 1 to 3 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms Y is selected from the group consisting of H, an alkyl group having 1 to 6 carbon atoms and an oligosaccharide consisting of 1 to 6 sugar monomers, and $R_9$ is selected from the group consisting of H, OH, and an oligosaccharide consisting of 1 to 6 sugar monomers.

11. A compound according to claim 9 wherein at least two of $R_1$, $R_2$, $R_3$, $R_4$, $R_5$, $R_6$, $R_7$, $R_8$ are each H or OH; the remaining functional groups are each independently selected from the group consisting of H; an alkyl group having 1 to 5 carbon atoms; an alkenyl group having 1 to 5 carbon atoms; a halogen-substituted alkyl group having 1 to 5 carbon atoms; OH; NR'R", wherein R' and R" are each independently H or an alkyl group having 1 to 3 carbon atoms; R NR"R''', wherein R' is an alkyl group having 1 to 3 carbon atoms and R" and R''' are each independently H or an alkyl group having 1 to 3 carbon atoms; ROH, wherein R is an alkyl group consisting of 1 to 3 carbon atoms; OR', wherein R' is an alkyl group having 1 to 3 carbon atoms; R'OR", wherein R' and R" are each independently an alkyl group having 1 to 2 carbon atoms; C(O)R', wherein R' is H or an alkyl group having 1 to 4 carbon atoms Y is selected from the group consisting of H, an alkyl group having 1 to 5 carbon atoms and an oligosaccharide consisting of 1 to 6 sugar monomers, and

$R_9$ is selected from the group consisting of H, OH, and an oligosaccharide consisting of 1 to 6 sugar monomers.

12. A compound according to claim 9 wherein at least two of the functional groups $R_1$, $R_2$, $R_3$, $R_4$, $R_5$, $R_6$, $R_7$, $R_8$ are OH.

13. A compound according to claim 9 wherein at least two of the functional groups $R_1$, $R_2$, $R_3$, $R_4$, $R_5$, $R_6$, $R_7$, $R_8$ are H.

14. A compound of the formula:

wherein X is NH,

R$_1$, R$_2$, R$_3$, R$_4$, R$_5$, R$_6$, R$_7$, R$_8$ are each independently selected from the group consisting of H; an alkyl group having 1 to 6 carbon atoms; an alkenyl group having 1 to 6 carbon atoms; an alkynyl group having 1 to 6 carbon atoms; a halogen-substituted alkyl group having 1 to 6 carbon atoms; OH; NR'R", wherein R' and R" are each independently H or an alkyl group having 1 to 3 carbon atoms; NR'C(O)R", wherein R' is H or an alkyl group having 1 to 3 carbon atoms and R" is an alkyl group having 1 to 2 carbon atoms; R'NR"R'", wherein R' is an alkyl group having 1 to 3 carbon atoms and R" and R'" are each independently H or an alkyl group having 1 to 3 carbon atoms; R'NR"C(O)R'", wherein R' is an alkyl group having 1 to 3 carbon atoms, R" is H or an alkyl group having 1 to 3 carbon atoms, and R'" is an alkyl group having 1 to 2 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; OC(O)NR'R", wherein R' and R" are each independently H or an alkyl group consisting of 1 to 3 carbon atoms; R'C(O)NR"R'", wherein R' is an alkyl group having 1 to 3 carbon atoms and R" and R'" are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; R'OC(O)R", wherein R' is an alkyl group having 1 to 3 carbon atoms, and R" is H or an alkyl group having 1 to 3 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms; a peptide consisting of 1 to 6 amino acids; and an oligosaccharide consisting of 1 to 6 sugar monomers, Y is selected from the group consisting of H, an alkyl group having 1 to 6 carbon atoms, a peptide consisting of 1 to 6 amino acids, and an oligosaccharide consisting of 1 to 6 sugar monomers, and R$_9$ is selected from the group consisting of H, an alkyl group having 1 to 6 carbon atoms; OH; NR'R", wherein R' and R" are each independently H or an alkyl group having 1 to 3 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; R'C(O)NR"R'", wherein R' is an alkyl group having 1 to 3 carbon atoms and R" and R'" are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; C(O)OR', wherein R' is H or an alkyl group having 1 to 4 carbon atoms; R'C(O)OR', wherein R' is an alkyl group having 1 to 4 carbon atoms and R" is H or an alkyl group having 1 to 4 carbon atoms; a peptide consisting of 1 to 6 amino acids; and an oligosaccharide consisting of 1 to 6 sugar monomers, or a pharmaceutically acceptable salt thereof.

15. A compound according to claim 14 wherein

R$_1$, R$_2$, R$_3$, R$_4$, R$_5$, R$_6$, R$_7$, R$_8$ are each independently selected from the group consisting of H; an alkyl group having 1 to 6 carbon atoms; an alkenyl group having 1 to 6 carbon atoms; an alkynyl group having 1 to 6 carbon atoms; a halogen-substituted alkyl group having 1 to 6 carbon atoms; OH; NR'R", wherein R' and R" are each independently H or an alkyl group having 1 to 3 carbon atoms; NR'C(O)R", wherein R' is H or an alkyl group having 1 to 3 carbon atoms and R" is an alkyl group having 1 to 2 carbon atoms; R'NR"R'", wherein R' is an alkyl group having 1 to 3 carbon atoms and R" and R'" are each independently H or an alkyl group having 1 to 3 carbon atoms; R'NR"C(O)R'", wherein R' is an alkyl group having 1 to 3 carbon atoms, R" is H or an alkyl group having 1 to 3 carbon atoms, and R'" is an alkyl group having 1 to 2 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; OC(O)NR'R", wherein R' and R" are each independently H or an alkyl group consisting of 1 to 3 carbon atoms; R'C(O)NR"R'", wherein R' is an alkyl group having 1 to 3 carbon atoms and R" and R'" are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; R'OC(O)R", wherein R' is an alkyl group having 1 to 3 carbon atoms, and R" is H or an alkyl group having 1 to 3 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms, Y is selected from the group consisting of H, an alkyl group having 1 to 6 carbon atoms and an oligosaccharide consisting of 1 to 6 sugar monomers, and R$_9$ is selected from the group consisting of H, OH, and an oligosaccharide consisting of 1 to 6 sugar monomers.

16. A compound according to claim 14 wherein

R$_1$, R$_2$, R$_3$, R$_4$, R$_5$, R$_6$, R$_7$, R$_8$ are each independently selected from the group consisting of H; an alkyl group having 1 to 5 carbon atoms; an alkenyl group having 1 to 5 carbon atoms; a halogen-substituted alkyl group having 1 to 5 carbon atoms; OH; NR'R", wherein R' and R" are each independently H or an alkyl group having 1 to 3 carbon atoms; R NR"R'", wherein R' is an alkyl group having 1 to 3 carbon atoms and R" and R'" are each independently H or an alkyl group having 1 to 3 carbon atoms; ROH, wherein R is an alkyl group consisting of 1 to 3 carbon atoms; OR', wherein R' is an alkyl group having 1 to 3 carbon atoms; R'OR", wherein R' and R" are each independently an alkyl group having 1 to 2 carbon atoms; C(O)R', wherein R' is H or an alkyl group having 1 to 4 carbon atoms;

Y is selected from the group consisting of H, an alkyl group having 1 to 5 carbon atoms and an oligosaccharide consisting of 1 to 6 sugar monomers, and $R_9$ is selected from the group consisting of H, OH, and an oligosaccharide consisting of 1 to 6 sugar monomers.

17. A compound according to claim 14 wherein at least two of the functional groups $R_1$, $R_2$, $R_3$, $R_4$, $R_5$, $R_6$, $R_7$, $R_8$ are OH and Y or $R_9$ is an oligosaccharide consisting of 1 to 6 sugar monomers.

18. A compound according to claim 14 wherein
at least two of the functional groups $R_1$, $R_2$, $R_3$, $R_4$, $R_5$, $R_6$, $R_7$, $R_8$ are H and Y or $R_9$ is an oligosaccharide consisting of 1 to 6 sugar monomers.

19. A compound of the formula:

wherein X is O, $R_1$, $R_2$, $R_3$, $R_4$, $R_5$, $R_6$, $R_7$, $R_8$ are each independently selected from the group consisting of H; an alkyl group having 1 to 6 carbon atoms; an alkenyl group having 1 to 6 carbon atoms; an alkynyl group having 1 to 6 carbon atoms; a halogen-substituted alkyl group having 1 to 6 carbon atoms; OH; NR'R", wherein R' and R" are each independently H or an alkyl group having 1 to 3 carbon atoms; NR'C(O)R", wherein R' is H or an alkyl group having 1 to 3 carbon atoms and R" is an alkyl group having 1 to 2 carbon atoms; RNR"R'", wherein R' is an alkyl group having 1 to 3 carbon atoms and R" and R'" are each independently H or an alkyl group having 1 to 3 carbon atoms; R'NR"C(O)R', wherein R' is an alkyl group having 1 to 3 carbon atoms, R" is H or an alkyl group having 1 to 3 carbon atoms, and R'" is an alkyl group having 1 to 2 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; OC(O)NR'R", wherein R' and R" are each independently H or an alkyl group consisting of 1 to 3 carbon atoms; R'C(O)NR"R'", wherein R' is an alkyl group having 1 to 3 carbon atoms and R" and R'" are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; R'OC(O)R", wherein R' is an alkyl group having 1 to 3 carbon atoms, and R" is H or an alkyl group having 1 to 3 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms; a peptide consisting of 1 to 6 amino acids; and an oligosaccharide consisting of 1 to 6 sugar monomers, Y is selected from the group consisting of H, an alkyl group having 1 to 6 carbon atoms, a peptide consisting of 1 to 6 amino acids, and an oligosaccharide consisting of 1 to 6 sugar monomers, and $R_9$ is selected from the group consisting of H, an alkyl group having 1 to 6 carbon atoms; OH; NR'R", wherein R' and R" are each independently H or an alkyl group having 1 to 3 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R wherein R' and R" are each independently H or an alkyl group consisting of 1 to 3 carbon atoms; R'C(O)NR"R'", wherein R' is an alkyl group having 1 to 3 carbon atoms and R" and R'" are each independently H or an alkyl group having 1 to 3 carbon atoms; C(O)R', wherein R' is H or an alkyl group having 1 to 4 carbon atoms; RC(O)R", wherein R' is an alkyl group having 1 to 4 carbon atoms, and R" is H or an alkyl group having 1 to 4 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms; a peptide consisting of 1 to 6 amino acids; and an oligosaccharide consisting of 1 to 6 sugar monomers, or a pharmaceutically acceptable salt thereof.

20. A compound according to claim 19 wherein $R_1$, $R_2$, $R_3$, $R_4$, $R_5$, $R_6$, $R_7$, $R_8$ are each independently selected from the group consisting of H; an alkyl group having 1 to 6 carbon atoms; an alkenyl group having 1 to 6 carbon atoms; an alkynyl group having 1 to 6 carbon atoms; a halogen-substituted alkyl group having 1 to 6 carbon atoms; OH; NR'R", wherein R' and R" are each independently H or an alkyl group having 1 to 3 carbon atoms; NR'C(O)R", wherein R' is H or an alkyl group having 1 to 3 carbon atoms and R" is an alkyl group having 1 to 2 carbon atoms; R'NR"R'", wherein R' is an alkyl group having 1 to 3 carbon atoms and R" and R'" are each independently H or an alkyl group having 1 to 3 carbon atoms; R'NR"C(O)RM, wherein R' is an alkyl group having 1 to 3 carbon atoms, R" is H or an alkyl group having 1 to 3 carbon atoms, and R'" is an alkyl group having 1 to 2 carbon atoms; ROH, wherein R is an alkyl group consisting of 1 to 3 carbon atoms; OR', wherein R' is an alkyl group having 1 to 4 carbon atoms; R'OR", wherein R' and R" are each independently an alkyl group having 1 to 4 carbon atoms; C(O)NR'R", wherein R' and R" are each independently H or an alkyl group consisting of 1 to 3 carbon atoms; OC(O)NR'R", wherein R' and R" are each independently H or an alkyl group consisting of 1 to 3 carbon atoms; R'C(O)NR"R'", wherein R' is an alkyl group having 1 to 3 carbon atoms and R" and R'" are each independently H or an alkyl group having 1 to 3 carbon atoms; C(O)R', wherein R' is H or an alkyl group having 1 to 4 carbon atoms; R'C(O)R", wherein R' is an alkyl group having 1 to 4 carbon atoms, and R" is H or an alkyl group having 1 to 4 carbon atoms; R'OC(O)R", wherein R' is an alkyl group having 1 to 3 carbon atoms, and R" is H or an alkyl group having 1 to 3 carbon atoms; C(O)OR', wherein R' is H or an alkyl group having 1 to 4 carbon atoms; R'C(O)OR", wherein R' is an alkyl group having 1 to 4 carbon atoms and R" is H or an alkyl group having 1 to 4 carbon atoms, Y is selected from the group consisting of H, an alkyl group having 1 to 6 carbon atoms and an oligosaccharide consisting of 1 to 6 sugar monomers, and $R_9$ is selected from the group consisting of H, OH, and an oligosaccharide consisting of 1 to 6 sugar monomers.

21. A compound according to claim 19 wherein $R_1$, $R_2$, $R_3$, $R_4$, $R_5$, $R_6$, $R_7$, $R_8$ are each independently selected from the group consisting of H; an alkyl group having 1 to 5 carbon atoms; an alkenyl group having 1 to 5 carbon atoms; a halogen-substituted alkyl group having 1 to 5 carbon atoms; OH; NR'R", wherein R' and R" are each independently H or an alkyl group having 1 to 3 carbon atoms; R'NR"R'", wherein R' is an alkyl group having 1 to 3 carbon atoms and R" end, R'" are each independently H or an alkyl group having 1 to 3 carbon atoms; ROH, wherein R is an alkyl group consisting of 1 to 3 carbon atoms; OR', wherein R' is an alkyl group having 1 to 3 carbon atoms; R'OR", wherein R' and R" are each independently an alkyl group having 1 to 2 carbon atoms; C(O)R', wherein R' is H or an alkyl group having 1 to 4 carbon atoms;

Y is selected from the group consisting of H, an alkyl group having 1 to 5 carbon atoms and an oligosaccharide consisting of 1 to 6 sugar monomers, and $R_9$ is selected from the group consisting of H, OH, and an oligosaccharide consisting of 1 to 6 sugar monomers.

22. A compound according to claim 19 wherein at least two of the functional groups $R_1$, $R_2$, $R_3$, $R_4$, $R_5$, $R_6$, $R_7$, $R_8$ are OH and Y or $R_9$ is an oligosaccharide consisting of 1 to 6 sugar monomers.

23. A compound according to claim 19 wherein at least two of the functional groups $R_1$, $R_2$, $R_3$, $R_4$, $R_5$, $R_6$, $R_7$, $R_8$ are H and Y or $R_9$ is an oligosaccharide consisting of 1 to 6 sugar monomers.

24. A compound according to claims 9, 10, 11, 12, 13, 14, 15, 16, 17, 18, 19, 20, 21, 22, or 23 that has an in vitro $IC_{50}$ toward human pancreatic or salivary α-amylase of less than $1 \times 10^{-4}$ M.

25. A compound according to claims 9, 10, 11, 12, 13, 14, 15, 16, 17, 18, 19, 20, 21, 22, or 23 that has an in vitro $IC_{50}$ toward human pancreatic or salivary α-amylase of less than $5 \times 10^{-4}$ M.

26. A method of inhibiting α-amylase enzyme activity in a human comprising administering an inhibitory effective amount of a compound according to 9, 10, 11, 12, 13, 14, 15, 16, 17, 18, 19, 20, 21, 22, or 23 having an in vitro $IC_{50}$ toward human pancreatic or salivary α-amylase of less than $1 \times 10^{-4}$ M to the human.

27. A method of inhibiting α-amylase enzyme activity in a human comprising administering an inhibitory effective amount of a compound according to claims 9, 10, 11, 12, 13, 14, 15, 16, 17, 18, 19, 20, 21, 22, or 23 demonstrating an in vitro $IC_{50}$ toward human pancreatic or salivary α-amylase of less than $5 \times 10^{-4}$ M to the human.

28. A compound according to claims 9, 10, 11, 12, 13, 14, 15, 16, 17, 18, 19, 20, 21, 22, or 23 wherein Y is an oligosaccharide consisting of at least 2 sugar monomers, $R_9$ is an oligosaccharide consisting of at least 2 sugar monomers, or Y and $R_9$ are an oligosaccharide consisting of at least 1 sugar monomer, and wherein the compound demonstrates a higher $IC_{50}$ toward α-amylase than toward other glucohydrolase enzymes.

29. The method of claim 1 where the in vitro $IC_{50}$ of the compound is less than $1 \times 10^{-6}$ M toward human salivary α-amylase enzyme.

30. The method of claim 1 where the in vitro $IC_{50}$ of the compound is less than $1 \times 10^{-8}$ M toward human pancreatic or human salivary α-amylase enzyme.

31. The method of claim 1 where the in vitro $IC_{50}$ of the compound is less than $1 \times 10^{-10}$ M toward human salivary α-amylase enzyme.

32. The method of claim 1 where the in vitro $IC_{50}$ of the compound is less than $5 \times 10^{-12}$ M toward human pancreatic or human salivary α-amylase enzyme.

* * * * *